(12) United States Patent
Zhou

(10) Patent No.: US 12,310,702 B2
(45) Date of Patent: May 27, 2025

(54) BLOOD PRESSURE MEASUREMENT MODULE, STRAP ASSEMBLY, AND WEARABLE DEVICE

(71) Applicant: GUANGDONG OPPO MOBILE TELECOMMUNICATIONS CORP., LTD., Guangdong (CN)

(72) Inventor: Shun Zhou, Guangdong (CN)

(73) Assignee: GUANGDONG OPPO MOBILE TELECOMMUNICATIONS CORP., LTD., Guangdong (CN)

( * ) Notice: Subject to any disclaimer, the term of this patent is extended or adjusted under 35 U.S.C. 154(b) by 98 days.

(21) Appl. No.: 18/325,362

(22) Filed: May 30, 2023

(65) Prior Publication Data
US 2023/0293030 A1 Sep. 21, 2023

Related U.S. Application Data

(63) Continuation of application No. PCT/CN2021/123165, filed on Oct. 12, 2021.

(30) Foreign Application Priority Data

Dec. 3, 2020 (CN) .......................... 202022862529.8

(51) Int. Cl.
*A61B 5/021* (2006.01)
*A61B 5/00* (2006.01)

(52) U.S. Cl.
CPC ........ *A61B 5/02141* (2013.01); *A61B 5/0002* (2013.01); *A61B 5/681* (2013.01)

(58) Field of Classification Search
CPC .... A61B 5/02141; A61B 5/0002; A61B 5/681
See application file for complete search history.

(56) References Cited

U.S. PATENT DOCUMENTS

| 2007/0279852 A1 | 12/2007 | Daniel et al. |
| 2015/0335284 A1 | 11/2015 | Nuovo et al. |

(Continued)

FOREIGN PATENT DOCUMENTS

| CN | 103536283 | 1/2014 |
| CN | 204520654 | 8/2015 |

(Continued)

OTHER PUBLICATIONS

EPO, Extended European Search Report for EP Application No. 21899721.1, Mar. 22, 2024.

(Continued)

*Primary Examiner* — Alexei Bykhovski
(74) *Attorney, Agent, or Firm* — Hodgson Russ LLP

(57) ABSTRACT

A blood pressure measurement module, a strap assembly, and a wearable device are provided. The blood pressure measurement module can be mounted on a strap of the wearable device. The blood pressure measurement module includes a housing, a measurement assembly and a wireless communication module. The housing is provided with an accommodation cavity, and the housing is connected to the strap. The measurement assembly is used for measuring the blood pressure, and the measurement assembly includes a light emitter and a light receiver. The light emitter and the light receiver are both arranged in the accommodation cavity. The light receiver is used for receiving the light that is emitted by the light emitter and reflected to the light receiver by a human body.

20 Claims, 7 Drawing Sheets

(56) References Cited

U.S. PATENT DOCUMENTS

| | | | |
|---|---|---|---|
| 2016/0324470 A1* | 11/2016 | Townsend | G06F 1/1679 |
| 2017/0011210 A1 | 1/2017 | Cheong et al. | |
| 2017/0055845 A1 | 3/2017 | Mirov et al. | |
| 2018/0027908 A1* | 2/2018 | Greenly | A61B 5/681 |
| 2018/0368701 A1* | 12/2018 | Vule | A61B 5/0205 |
| 2019/0133464 A1* | 5/2019 | Fish | A61B 5/681 |
| 2020/0015748 A1* | 1/2020 | Kline | G01H 11/08 |
| 2021/0278561 A1* | 9/2021 | Mehra | G04G 21/025 |
| 2021/0345939 A1* | 11/2021 | Jumbe | H04R 1/028 |
| 2022/0128950 A1* | 4/2022 | Trapero Martin | A61B 5/6833 |

FOREIGN PATENT DOCUMENTS

| | | | | |
|---|---|---|---|---|
| CN | 205625904 | 10/2016 | | |
| CN | 106102565 | 11/2016 | | |
| CN | 106527106 | 3/2017 | | |
| CN | 206877213 | 1/2018 | | |
| CN | 207837535 | 9/2018 | | |
| CN | 109009055 | 12/2018 | | |
| CN | 109662699 | 4/2019 | | |
| CN | 109907438 | 6/2019 | | |
| CN | 211213127 | 8/2020 | | |
| CN | 213821398 | 7/2021 | | |
| EP | 3072441 | 9/2016 | | |
| EP | 3459447 A2 * | 3/2019 | | A61B 5/02427 |
| EP | 3498160 | 6/2019 | | |
| WO | WO-2016031221 A1 * | 3/2016 | | A61B 5/0048 |
| WO | 2019071878 | 4/2019 | | |

OTHER PUBLICATIONS

WIPO, International Search Report and Written Opinion for PCT/CN2021/123165, Jan. 17, 2022.

CNIPA, Notification to Grant Patent Right for Invention for CN Application No. 202022862529.8, Sep. 24, 2021.

* cited by examiner

BLOOD PRESSURE MEASUREMENT MODULE, STRAP ASSEMBLY, AND WEARABLE DEVICE

CROSS-REFERENCE TO RELATED APPLICATIONS

The present disclosure is a continuation of International Application No. PCT/CN2021/123165, filed Oct. 12, 2021, which claims priority to Chinese Patent Application No. 202022862529.8, filed Dec. 3, 2020, the entire disclosures of which are incorporated herein by reference.

TECHNICAL FIELD

The present disclosure relates to the technical field of wearable devices, and in particular to a blood pressure measurement module, a strap assembly and a wearable device.

BACKGROUND

A wearable device such as a smart watch generally include a strap and an electronic device, and the strap is used to wear the electronic device to a user's wrist. The electronic device is generally provided with a blood pressure measurement component. After the smart watch is worn on the user's wrist, the electronic device can measure a user's blood pressure to provide health guidance. The blood pressure measurement component needs to occupy an internal installation space of the electronic device, which is not conducive to a thinner and lighter design of the electronic device.

SUMMARY

Based on this, it is necessary to provide a blood pressure measurement module, a strap assembly and a wearable device.

In an aspect, the present disclosure provides a blood pressure measurement module, configured to install on a strap of a wearable device, and the blood pressure measurement module includes:
- a housing, provided with an accommodation cavity, the housing being configured to connect to the strap;
- a measurement assembly, configured to measure a blood pressure and including: a light emitter and a light receiver, where the light emitter and the light receiver are disposed in the accommodation cavity, and the light receiver is configured to receive light emitted from the light emitter and reflected by a human body; and
- a wireless communication module, communicatively connected to the measurement assembly, where the wireless communication module is configured to perform wireless communication connection with an external device or an electronic device of the wearable device.

In another aspect, the present disclosure provides a strap assembly, configured to connect to an electronic device of a wearable device. The strap assembly includes a strap and the above-described blood pressure measurement module, and the strap is connected to the electronic device.

In a still another aspect, the preset disclosure provides a wearable device, including an electronic device and the above-described strap assembly, the strap assembly is configured to wear the electronic device on a user's wrist, thereby to make an emitting end of the light emitter face away from a user's wrist.

BRIEF DESCRIPTION OF THE DRAWINGS

In order to more clearly explain embodiments of the present disclosure or the technical scheme in the related art, the drawings needed to be used in the description of the embodiments or the related art will be briefly introduced below. Apparently, the drawings in the following description are only some of the embodiments of the present disclosure, and other drawings can be obtained according to these drawings without creative work for those skilled in the art.

Figure 1:
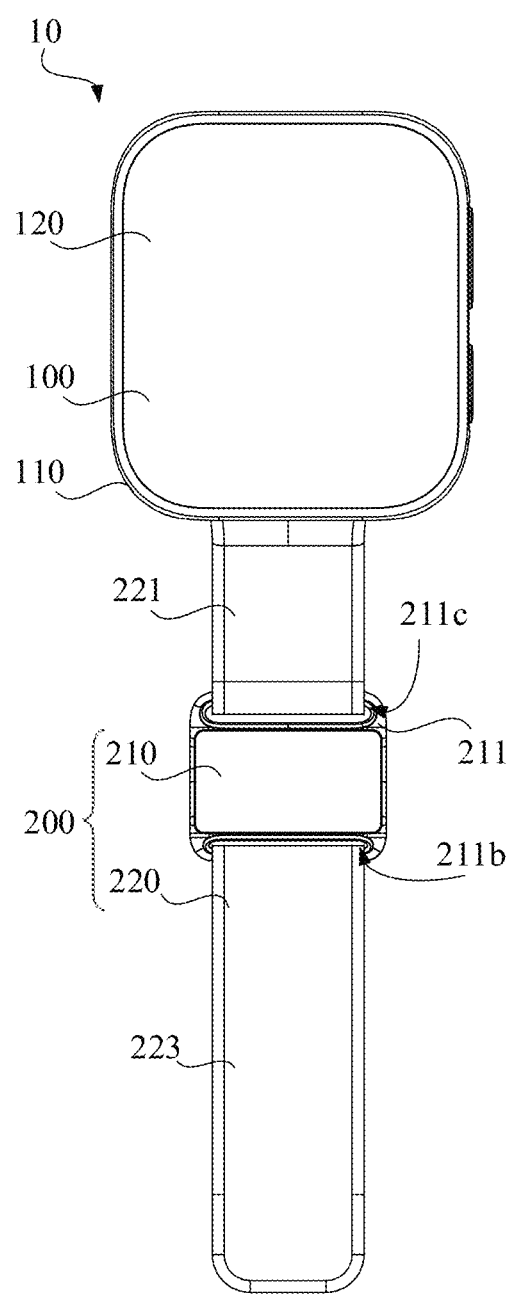
FIG. 1 illustrates a schematic diagram of a wearable device according to an embodiment.

DESCRIPTION OF REFERENCE NUMERALS 10, wearable device
100, electronic device
103, card slot
110, middle frame
120, display module
130, back cover
200, strap assembly
210, blood pressure measurement module
211, housing
211a, accommodation cavity
211b, through hole
211c, installation groove
2113, bearing member
2113a, frame body
2113b, bottom cover
2113c, penetrating hole
2115, cover plate
2115a, base plate
A1, light transmission area
A2, optical texture structure
2115b, light shielding part
213, measurement assembly
2131, light emitter
2133, light receiver
214, wireless communication module
215, circuit board
217, battery
18, partition member
218a, first hole
218b, second hole
2191, charging terminal -continued 2193, magnetic attraction member
2195, sealing ring
220, strap
221, first section
223, second section

DETAILED DESCRIPTION OF EMBODIMENTS

In order to facilitate the understanding of the present disclosure, the present disclosure will be described more comprehensively with reference to the relevant drawings. Alternative embodiments of the present disclosure are illustrated in the drawings. However, the present disclosure can be implemented in many different forms and is not limited to the embodiments described herein. On the contrary, these embodiments are provided to make the present disclosure more thorough and comprehensive.

Figure 2:
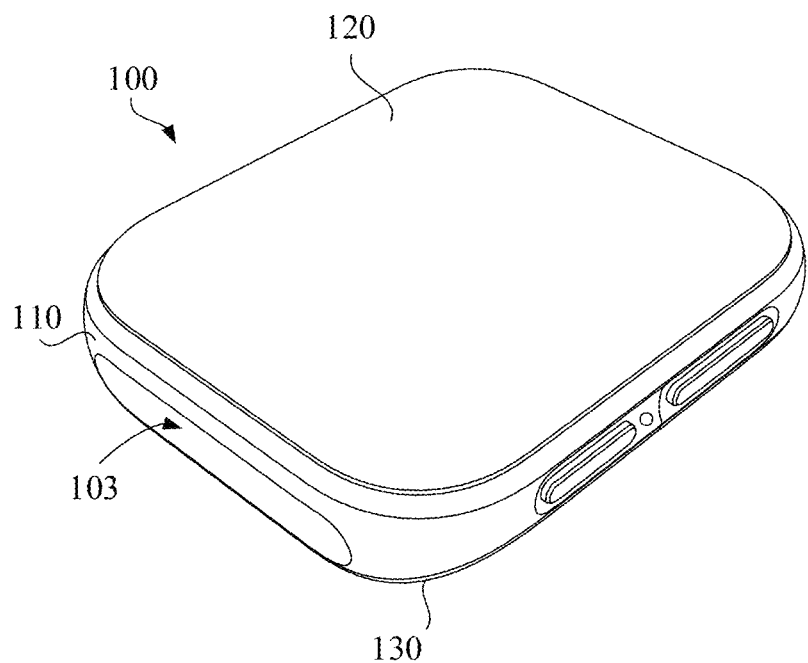
FIG. 2 illustrates a schematic diagram of an electronic device of a wearable device according to an embodiment.

As illustrated in FIG. 1, in some embodiments, a wearable device 10 includes an electronic device 100 and a strap assembly 200, which is installed to the electronic device 100 and can be worn to a user's wrist through the strap assembly 200. As illustrated in FIG. 2, the electronic device 100 includes a middle frame 110, and electronic components such as a circuit board (not illustrated in figure) and a power supply module (not illustrated in figure) disposed in the middle frame 110. The middle frame 110 is provided with an installation cavity, and the electronic components such as the circuit board and the power supply module are disposed in the installation cavity. The middle frame 110 can be made of a nonmetallic material such as plastic, rubber, silica gel, wood, ceramics or glass. The middle frame 110 can be made of a metallic material such as stainless steel, aluminum alloy or magnesium alloy. The middle frame 110 can be a metal injection-molded component, that is, a structural rigidity of the middle frame 110 is ensured by using the metallic material, and an inner surface of a metal body is formed with protrusions, grooves, threaded holes and other structures for assembly and positioning by injection molding.

In some embodiments, the wearable device 10 is a smart watch, and the installation cavity of the middle frame 110 is configured to install electronic components such as a power supply module, a circuit board, a display module 120, a biosensor, etc. The circuit board can integrate electronic components such as a processor, a storage unit and a communication module of the wearable device 10, and the power supply module (such as a lithium battery) can supply power to the circuit board, the display module 120 and other electronic components. The display module 120 covers the installation cavity and is connected to the middle frame 110, which can be configured to display information and provide an interactive interface for users. The display module 120 may further include a display screen and a front cover covering the display screen. The display screen may be a liquid crystal display (LCD) screen or an organic light-emitting diode (OLED) screen, and the front cover may be a glass cover or a sapphire cover. The front cover is transparent and has relatively high light transmittance, in some embodiments, a light transmittance of the front cover is above 80%. The display module 120 may have a touch function, but the touch function is not necessary, and neither is the display module 120.

In some embodiment, the electronic device 100 may include a back cover 130 connected to the middle frame 110, and at least part of a surface of the back cover 130 is attached to the user's wrist after the wearable device 10 is worn on the user's wrist. In the embodiment where the electronic device 100 includes the display module 120, the back cover 130 and the display module 120 are opposite to each other and disposed on two ends of the middle frame 110, and cover two ends of the the installation cavity. The back cover 130 may be made of glass, ceramic or plastic, and may be provided with a measurement window for measurement of a biosensor such as a heart rate sensor. Of course, in some embodiments, the back cover 130 may be integrally formed with the middle frame 110. The electronic device 100 may include more than two kinds of biosensors, which can be configured to detect biological data such as heart rate, respiratory rate or body fat. In some embodiments, the biosensors can be configured to detect motion states, such as for step counting. In other embodiments, the wearable device 10 may be a smart bracelet or the like.

The middle frame 110 is a rectangular frame, and four corners of the rectangle can be processed into arc transition by chamfering process, thus the wearable device 10 has better appearance characteristics. In other embodiments, the middle frame 110 may have a circular frame shape. A side surface of the middle frame 110 (that is, a surface of the middle frame 110 facing away from the installation cavity) may be provided with a matching structure for installing the strap assembly 200, and the strap assembly 200 can form a reliable connection with the middle frame 110 through the matching structure, so as to reliably wear the electronic device 100 to the user's wrist. In some embodiments, the strap assembly 200 can be conveniently detached from the middle frame 110, thus the user can conveniently replace the strap assembly 200. In some embodiments, users can purchase various styles of strap assemblies 200, and replace the strap assemblies 200 according to the usage scenarios, so as to improve the convenience of use. In some embodiments, users can use the more formal strap assembly 200 in formal occasions, and use the casual strap assembly 200 in recreational occasions.

As illustrated in FIGS. 1 and 2, in some embodiments, the strap assembly 200 includes a blood pressure measurement module 210 and two straps 220 (one of the straps is illustrated in FIG. 1), and the blood pressure measurement module 210 is installed to one of the straps 220. Two opposite ends of the electronic device 100 are respectively provided with card slots 103, and an end of each of the two straps 220 is connected with the electronic device 100, and an end of each of the two straps 220 facing away from the electronic device 100 can be buckled to define an accommodation space, thus the electronic device 100 can be worn on the user's wrist through the two straps 220. In other embodiments, the strap 220 can be a whole-section structure, an end of the strap 220 is connected to an end of the electronic device 100, and another end of the electronic device 100 can be provided with a snap ring for the strap 220 to pass through, and a free end of the strap 220 can pass through and bypass the snap ring and then be fixed to another position of the strap 220 to form an accommodation space, and a size of the accommodation space is easy to adjust for the convenience of users.

Figure 3:
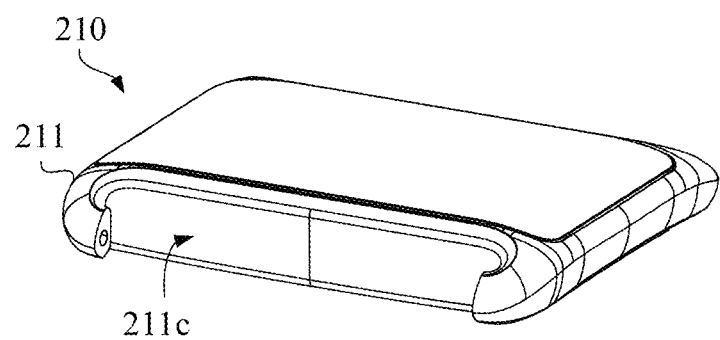
FIG. 3 illustrates a schematic diagram of a blood pressure measurement module of a wearable device according to an embodiment.
Figure 4:
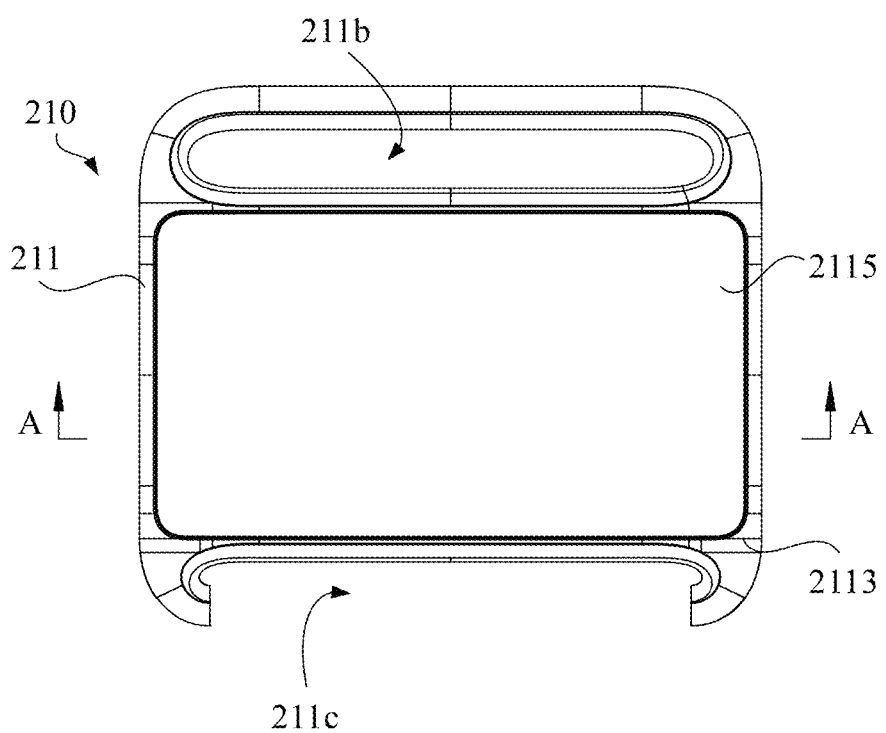
FIG. 4 illustrates a front view of the blood pressure measurement module of the wearable device illustrated in FIG. 3.
Figure 5:
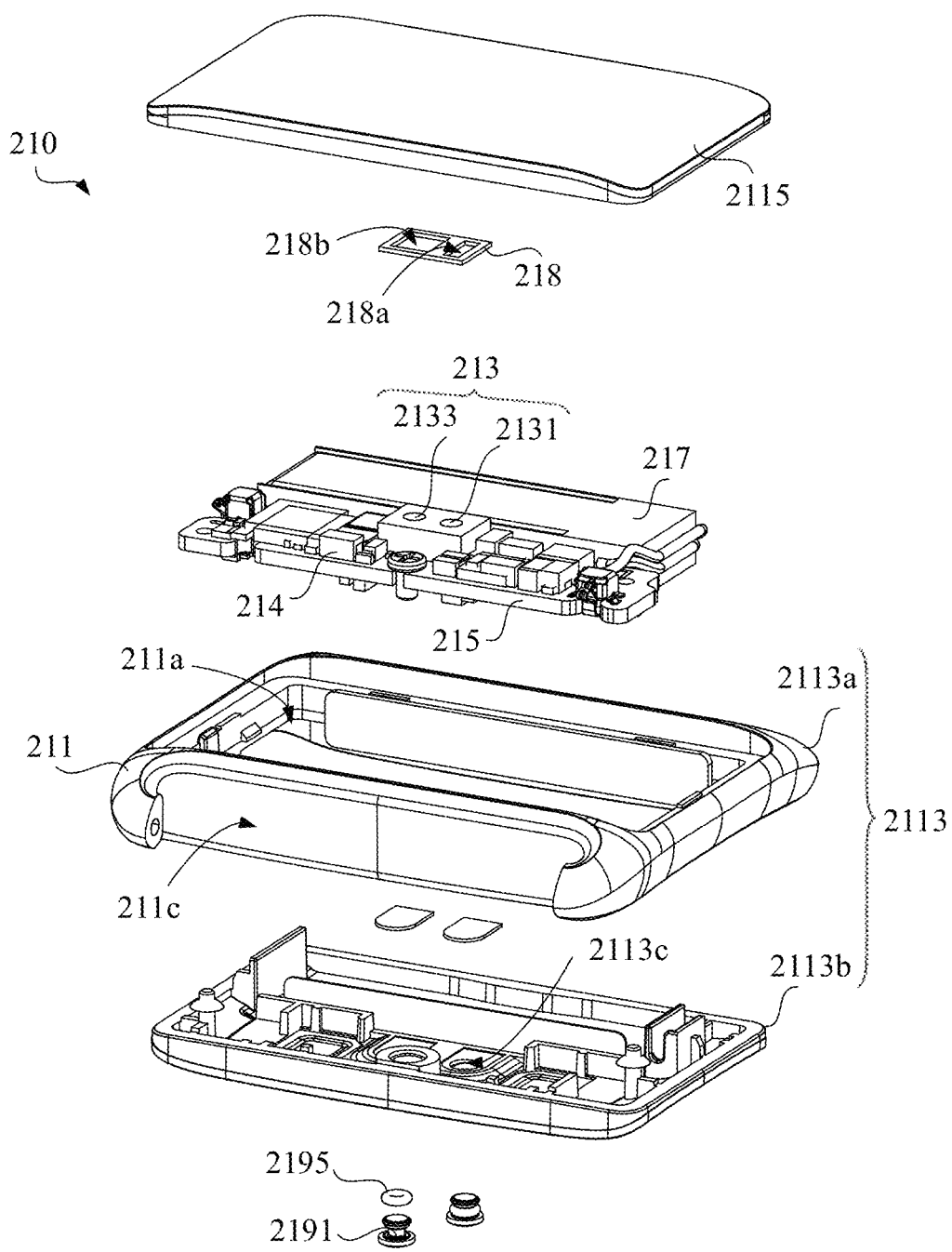
FIG. 5 illustrates an exploded view of the blood pressure measurement module of the wearable device illustrated in FIG. 3.

As illustrated in FIGS. 3, 4 and 5, the blood pressure measurement module 210 includes a housing 211, a measurement assembly 213 and a wireless communication module 214. The measurement assembly 213 and the wireless communication module 214 are both arranged in the housing 211. The measurement assembly 213 can be configured to measure a blood pressure of the user and transmit the measurement data to the electronic device 100 or an external device such as a mobile phone and a tablet computer through the wireless communication module 214. In this embodiment, the housing 211 has a rectangular block shape, the housing 211 is provided with an accommodation cavity 211a, and the housing 211 is configured to connect the strap 220. In other embodiments, the housing 211 can be in the shape of a circular block or a racetrack, the racetrack refers to a figure formed by two opposite sides of a rectangle circumscribed by semicircles respectively.

As illustrated in FIG. 4 in conjunction with FIG. 1, in this embodiment, an end of the housing 211 is provided with a through hole 211b, and an opposite end of the housing 211 is provided with an installation groove 211c configured to connect the strap 220, and the through hole 211b is configured to thread the strap 220. The strap 220 may include a first section 221 and a second section 223, an end of the first section 221 is connected to the electronic device 100, an opposite end of the first section 221 is connected to the installation groove 211c of the housing 211, the second section 223 is connected to an opposite end of the housing 211.

In some embodiments, an end of the second section 223 can be connected to the end of the electronic device 100 facing away from the first section 221, and a free end of the second section 223 can pass through the through hole 211b of the housing 211, bypass the end of the housing 211 facing away from the installation groove 211c, and then be fixed to another position of the second section 223. In some embodiments, the free end of the second section 223 can be provided with a snap, and the second section 223 can be provided with a plurality of snapping holes at intervals along its length direction. After the snap is snapped into one of the snapping holes, the free end of the second section 223 can be fixed, thus the size of the accommodation space for threading the user's wrist can be easily adjusted. Of course, the second section 223 can be provided with a magnetic piece, and the second section 223 can be provided with a plurality of magnetic attraction fitting pieces along its length direction, and the free end of the second section 223 can be fixed by attracting the magnetic attraction fitting piece and the magnetic piece. The magnetic piece can be a magnet, the magnetic attraction fitting piece can be a magnet, or a magnetic metal piece such as iron, cobalt, nickel and any one of their alloys.

Of course, in other embodiments, the wearable device 10 may include another strap 220, and the another strap 220 is connected to the opposite end of the electronic device 100, and the second section 223 can form the accommodation space for threading the user's wrist in cooperation with the another strap 220.

Figure 6:
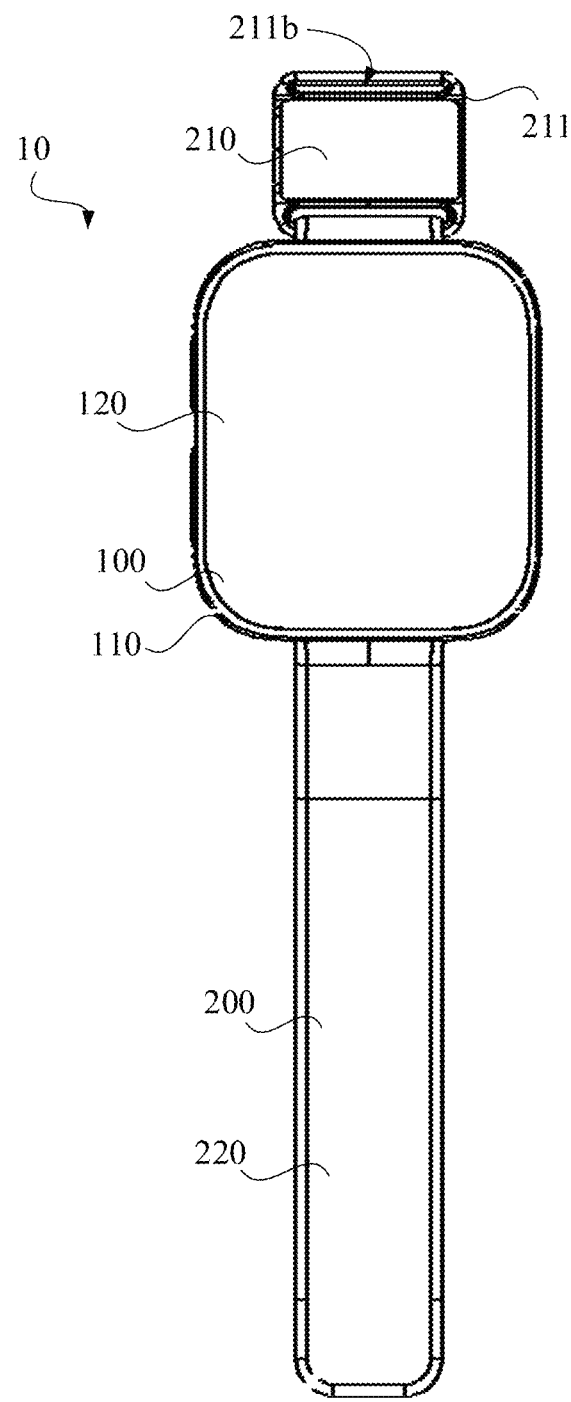
FIG. 6 illustrates a schematic diagram of a wearable device according to another embodiment.

As illustrated in FIG. 6, in other embodiments, the housing 211 can be directly connected to the electronic device 100. In some embodiments, the housing 211 of the blood pressure measurement module 210 can be detachably connected to the middle frame 110 of the electronic device 100. In other words, an end of the housing 211 is configured to connect to the electronic device 100, and an opposite end of the housing 211 is configured to connect to the strap 220. In this embodiment, the housing 211 of the blood pressure measurement module 210 and the middle frame 110 of the electronic device 100 can be provided with corresponding matching structures, so as to realize the convenient disassembly of the blood pressure measurement module 210 and the electronic device 100. In some embodiments, the middle frame 110 of the electronic device 100 can be provided with a telescopic thimble, and the housing 211 of the blood pressure measurement module 210 is provided with a connection hole. The thimble can be inserted into the connection hole to realize the assembly of the electronic device 100 and the blood pressure measurement module 210, and the thimble can be withdrawn from the connection hole to detach the blood pressure measurement module 210 from the electronic device 100.

In other embodiments, two opposite ends of the housing 211 may be provided with through holes 211b, and the through holes 211b are configured to thread the strap 220, thus the blood pressure measurement module 210 can be slidably arranged on the strap 220. In other words, in this embodiment, the strap 220 can be threaded through the through hole 211b at an end of the housing 211 and then passed through the through hole 211b at an opposite end of the housing 211, and the blood pressure measurement module 210 can be slidably installed on the strap 220. This embodiment can conveniently adjust a position of the blood pressure measurement module 210 on the strap 220, facilitate the assembly of the blood pressure measurement module 210 and the strap 220, and easily realize the detachment of the blood pressure measurement module 210 from the strap 220. In other embodiments, other structures can be adopted to realize the convenient disassembly and assembly of the blood pressure measurement module 210 and the strap 220, so as to improve the convenience of use.

As illustrated in FIG. 5, the measurement assembly 213 includes a light emitter 2131 and a light receiver 2133, both of which are arranged in the accommodation cavity 211a, and the light receiver 2133 is configured to receive light emitted by the light emitter 2131 and reflected by a human body to the light receiver 2133. In this embodiment, the light emitter 2131 includes an LED light source. The light emitter 2131 emits infrared rays from an emitting end, and the infrared rays pass through the housing 211 and enter the human body. After being absorbed and reflected by human blood vessels and tissues, the infrared rays pass through the housing 211 and enter a receiving end of the light receiver 2133. By using photoplethysmographic (PPG), a blood pressure can be calculated. Of course, in other embodiments, the light source of the light emitter 2131 can adopt other forms, for example, the light emitter 2131 can adopt a light source capable of emitting white light.

In this embodiment, the blood pressure measurement module 210 further includes a circuit board 215 and a battery 217 electrically connected to the circuit board 215. Both the circuit board 215 and the battery 217 are disposed in the accommodation cavity 211a, and both the light emitter 2131 and the light receiver 2133 are electrically connected to the circuit board 215. The battery 217 is configured to supply power to the blood pressure measurement module 210 and other electronic components on the circuit board 215. The wireless communication module 214 of the blood pressure measurement module 210 is communicably connected to the measurement assembly 213, and the battery 217 can further supply power to the wireless communication module 214. In some embodiments, the wireless communication module 214 can be configured to perform wireless communication connection with the electronic device 100 of the wearable device 10 to transmit the measurement data of the blood pressure measurement module 210 to the electronic device 100. Of course, in some embodiments, the wireless communication module 214 can directly communicate wirelessly with an external device such as a mobile phone, a tablet computer and another terminal, and transmit the measurement data of the blood pressure measurement module 210 to the external device.

The wireless communication module 214 may have various forms. In some embodiments, the wireless communication module 214 may be a Bluetooth communication module, a wireless fidelity (Wi-Fi) communication module, an infrared data association (IrDA) module, a ZigBee communication module, an ultra wideband (UWB) module, a near field communication (NFC) module, etc.

In the embodiment where the strap assembly 200 is detachably connected to the electronic device 100, the user can detach the strap assembly 200 from the wearable device 10 and attach the blood pressure measurement module 210 to a body part such as a neck, an ear or a fingertip for blood pressure measurement. Compared with the related art in which blood pressure is measured on a wrist and the wearable device 10 is required to wear well, the blood pressure measurement module 210 of this embodiment can transmit blood pressure measurement data to the external device or the electronic device 100 of the wearable device 10 through the wireless communication module 214, thus improving the flexibility of measurement. Compared with the related art of measuring blood pressure at the wrist, the blood pressure measurement module 210 of this embodiment can obtain more accurate blood pressure measurement values by measuring blood pressure at the neck, the ear or the fingertip, thus the accuracy of the blood pressure measurement can be improved.

Of course, it can be understood that since the blood pressure measurement module 210 of the present disclosure is no longer integrated with the electronic device 100 of the wearable device 10, an internal installation space of the electronic device 100 can be saved, which is beneficial to the thinner and lighter design of the electronic device 100. Moreover, since the blood pressure measurement module 210 is no longer integrated into the electronic device 100 of the wearable device 10, the light emitter 2131 and the light receiver 2133 are no longer limited by the installation space of the electronic device 100, thus the blood pressure measurement assembly 213 with stronger performance can be adopted to improve the accuracy of blood pressure measurement. Of course, it can be understood that the blood pressure measurement module 210 of the present disclosure can measure the blood pressure at the wrist of the user, and can also improve the accuracy of the measurement.

Of course, it can be understood that the strap assembly 200 may not be detached from the electronic device 100 during the blood pressure measurement of the user, so as to save the time for disassembling the strap assembly 200 and improve the convenience of use. In this embodiment, the strap assembly 200 need not be configured to be easily detached from the electronic device 100. In this embodiment, the battery 217 or the circuit board 215 of the blood pressure measurement module 210 can be defaulted, in some embodiments, a power supply module of the electronic device 100 can be used to supply power to the blood pressure measurement module 210.

In the embodiment where the strap 220 is detachably connected to the housing 211 of the blood pressure measurement module 210, the user can detach the blood pressure measurement module 210 from the strap 220 and attach the blood pressure measurement module 210 to a body part such as a neck, an ear or a fingertip for blood pressure measurement. In the blood pressure measurement module 210 of this embodiment, the strap 220 does not need to be detached from the electronic device 100 when the user measures blood pressure through the blood pressure measurement module 210, and the strap 220 does not need to move with the blood pressure measurement module 210, thus the convenience of use can be improved, and the flexibility and accuracy of blood pressure measurement can also be improved.

The blood pressure measurement module 210 is connected to the strap 220 through the housing 211, and the blood pressure measurement module 210 measures the blood pressure by using the light emitter 2131 and the light receiver 2133. After the blood pressure measurement module 210 is separated from the electronic device 100, the blood pressure measurement module 210 can wirelessly communicate with an external device such as a mobile phone or a tablet computer through the wireless communication module 214, or wirelessly communicate with the electronic device 100 of the wearable device 10 through the wireless communication module 214. The user can remove the wearable device 10 from the wrist and attach the blood pressure measurement module 210 to the neck, the ear, the fingertip and another body part for blood pressure measurement, so as to obtain more accurate blood pressure measurement results. In other words, the above-mentioned blood pressure measurement module 210 is no longer integrated into the electronic device 100 of the wearable device 10, and the blood pressure can be accurately measured without being in good condition, thus the flexibility and accuracy of the blood pressure measurement can be improved.

As illustrated in FIG. 5, the housing 211 includes a bearing member 2113 and a cover plate 2115. The cover plate 2115 covers an emitting end of the light emitter 2131 and a receiving end of the light receiver 2133, and the cover plate 2115 encloses with the bearing member 2113 to define the accommodation cavity 211a. After the light emitter 2131 emits infrared rays from the emitting end, the infrared rays pass through the housing 211 and enter the human body, are absorbed and reflected by human blood vessels and tissues, and then enter the receiving end of the light receiver 2133 through the cover plate 2115.

In this embodiment, after the electronic device 100 is worn on the user's wrist, the emitting end of the light emitter 2131 faces away from the user's wrist. In other words, after the electronic device 100 is worn on the user's wrist, the cover plate 2115 is located on a side of the housing 211 facing away from the wrist. In the process of measuring blood pressure, the user can directly attach the fingertip of the other hand to the cover plate 2115 without removing the wearable device 10 from the wrist, so as to measure blood pressure, thereby improving the convenience of use. Of course, in this embodiment, the user can attach the blood pressure measurement module 210 to another part of the body, such as the neck or the ear, to measure blood pressure, which can also improve the convenience of measurement.

Of course, in other embodiments, after the electronic device 100 is worn on the user's wrist, the emitting end of the light emitter can face towards the user's wrist, that is, the cover plate 2115 is attached to the user's wrist. In this embodiment, the blood pressure measurement module 210 can measure the blood pressure of the user in real time to improve the convenience of use. Especially, for patients suffering from blood pressure-related diseases or people at risk, such as the elderly or hypertensive patients, the blood pressure measurement module 210 of this embodiment can measure the blood pressure in real time and provide health reminders in time.

Figure 7:
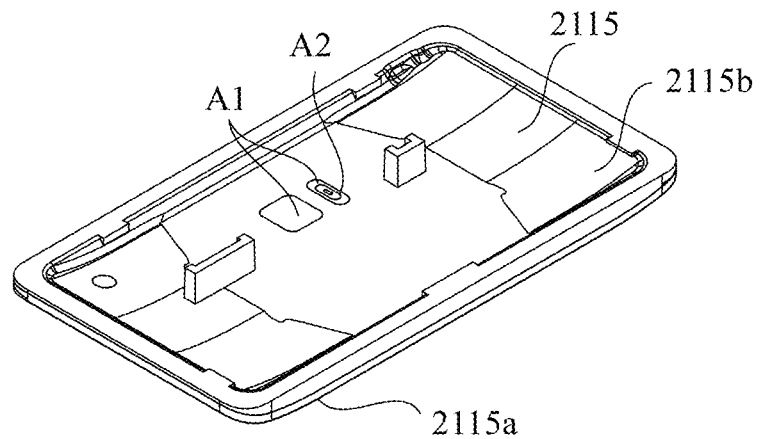
FIG. 7 illustrates a schematic diagram of a cover plate of a blood pressure measurement module according to an embodiment.

As illustrated in FIG. 7, in this embodiment, the cover plate 2115 includes a base plate 2115a and a light shielding part 2115b connected to the base plate 2115a, and the light shielding part 2115b defines light transmission areas A1 of the base plate 2115a, and the light transmission areas A1 cover the emitting end of the light emitter 2131 and the receiving end of the light receiver 2133, respectively. In some embodiments, the light shielding part 2115b forms a racetrack-shaped boundary, and the base plate 2115a is filled in an area surrounded by the racetrack-shaped boundary, thus the light transmission areas A1 of the base plate 2115a are defined by the boundary of the light shielding part 2115b. In other embodiments, the light shielding part 2115b can be provided with a through hole, and a hole wall of the through hole can be used as a boundary to define the light transmission areas A1 of the base plate 2115a. The light transmission areas A1 have a relatively high light transmittance, in some embodiment, the light transmittance of the light transmission area A1 can be above 85%. The light shielding part 2115b has a relatively low light transmittance, in some embodiments, the light transmittance of the light shielding part 2115b can be below 40%, so as to shield other electronic components in the blood pressure measurement module 210 by the light shielding part 2115b, and to avoid the interference of ambient light on the light receiver 2133 and influence the accuracy of blood pressure measurement results.

In this embodiment, the base plate 2115a and the light shielding part 2115b are injection molded in two colors. In other words, the base plate 2115a and the light shielding part 2115b are directly molded by injection molding to form a reliable connection. The color of the molded base plate 2115a is different from that of the light shielding part 2115b. In some embodiments, the base plate 2115a is made of polycarbonate (PC), and the light shielding part 2115b is made of acrylonitrile butadiene styrene (ABS). After injection molding, the base plate 2115a is transparent and the light shielding part 2115b is black. In other embodiments, the base plate 2115a is made of PC 141R, and the base plate 2115a after injection molding has the advantages of high transparency and strong fracture resistance. The light shielding part 2115b is made of PC, and the light shielding part 2115b after injection molding is black, so as to play a better light shielding effect.

In this embodiment, each light transmission area A1 is closed in a circumferential direction, and the light transmission areas A1 are located in a middle area of the cover plate 2115, thus the blood pressure measurement module 210 has a relatively good appearance effect. In the process of measuring blood pressure, this structural arrangement can better attach the cover plate 2115 to a body surface, thus the light transmission areas A1 can be reliably attached to the skin, thereby improving the accuracy of measurement. In some embodiments, a surface of the base plate 2115a facing away from the light shielding part 2115b has a 3D structure (as illustrated in FIG. 3), which may include a planar area and curved areas. The planar area is located in a middle of the base plate 2115a, and the curved areas extends from edges of the planar area, and two ends of the planar area are provided with the curved areas, thus better appearance characteristics can be obtained. The light transmission areas A1 are located in the planar area, and the light transmission areas A1 can be reliably attached to the skin to improve the accuracy of blood pressure measurement.

Figure 8:
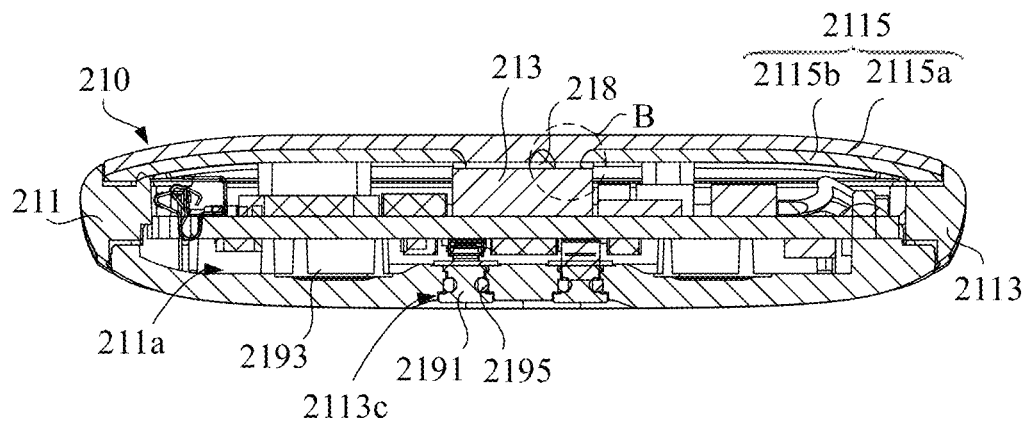
FIG. 8 illustrates a cross-sectional view of the blood pressure measurement module illustrated in FIG. 4 taken along a line A-A.
Figure 9:
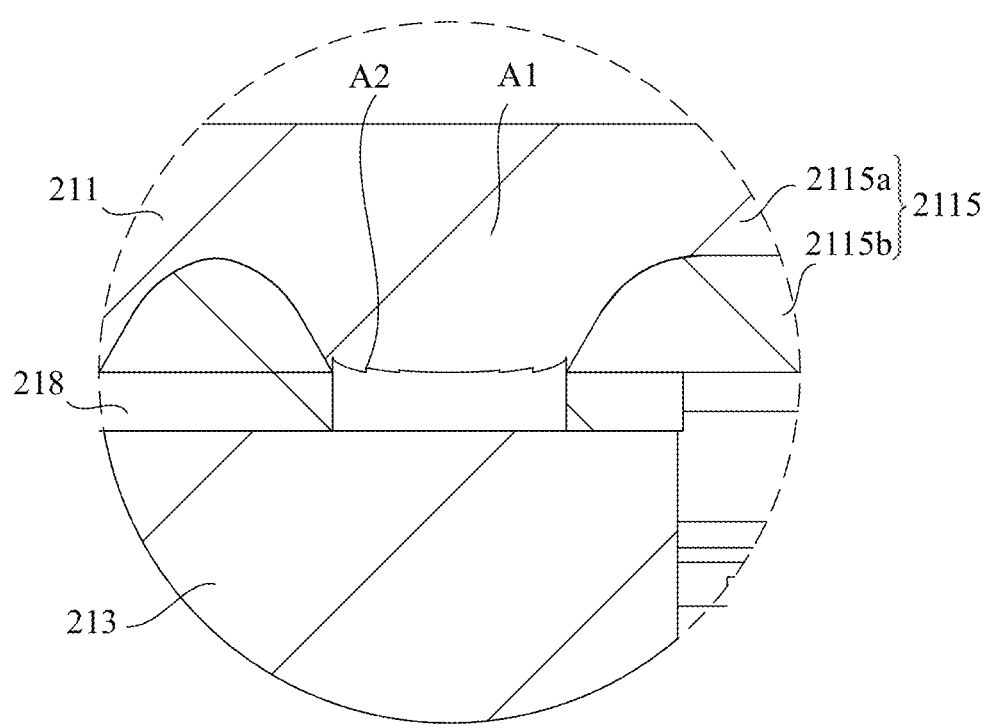
FIG. 9 illustrates an enlarged schematic view at a position B of the blood pressure measurement module illustrated in FIG. 8.

As illustrated in FIGS. 8 and 9, in this embodiment, one of the light transmission areas A1 is provided with an optical texture structure A2, which covers the emitting end of the light emitter 2131 and is configured to gather light of the light emitter 2131. The light gathering function of the optical texture structure A2 can reduce the dissipation of light energy, thus the energy of light can be concentrated in a small area as much as possible, thus avoiding the relatively high irrelevant loss of light after reflection and refraction due to dispersion, and improving the accuracy of blood pressure measurement.

In some embodiments, the optical texture structure A2 and the corresponding portion of the base plate 2115a form a Fresnel lens. The Fresnel lens can reduce a thickness of the base plate 2115a where the optical texture structure A2 is located. In some embodiments, the thickness of the base plate 2115a where the optical texture structure A2 is located is about 0.5 mm. In other words, a vertical distance between a tip of the optical texture structure A2 and an appearance surface of the base plate 2115a is about 0.5 mm. In some embodiments, both the light shielding part 2115b and the optical texture structure A2 are located on a side of the base plate 2115a facing towards the light emitter 2131. The vertical distance between the tip of the optical texture structure A2 and the surface of the base plate 2115a facing away from the light emitter 2131 is about 0.5 mm. In the above embodiment, the light transmission area A1 where the optical texture structure A2 is located has a better light-gathering effect and a thinner thickness, and is easy to process and shape. The light transmission area A1 where the optical texture structure A2 is located can not only obtain better light-gathering effect, but also realize thinner design to reduce the loss of light energy, so as to further improve the accuracy of blood pressure measurement. In other embodiments, the optical texture structure A2 and the corresponding portion of the base plate 2115a can also form another type of optical lenses, such as a convex lens, so as to obtain a light-gathering effect, which will not be described in detail here.

As illustrated in FIG. 5, in this embodiment, the blood pressure measurement module 210 includes a partition member 218, which is arranged at the light transmission areas A1 to partition the emitting end of the light emitter 2131 and the receiving end of the light receiver 2133, so as to avoid light mixing and interference between an emitting light path of the light emitter 2131 and a receiving light path of the light receiver 2133, thereby reducing the accuracy of blood pressure measurement.

Specifically, in this embodiment, the partition member 218 is made of foam, and has a first hole 218a and a second hole 218b arranged at intervals, a side of the partition member 218 abuts against the cover plate 2115, and an opposite side of the partition member 218 abuts against at least one of the light emitter 2131 and the light receiver 2133, with the first hole 218a corresponding to the emitting end of the light emitter 2131 and the second hole corresponding to the receiving end of the light receiver 2133. In other embodiments, the partition member 218 may be one of a rubber member, a silicone member, and a plastic member with low light transmittance.

The partition member 218 can prevent mixed light from being generated between the emitting light path of the light emitter 2131 and the receiving light path of the light receiver 2133, and can also play a buffering role between the measurement assembly 213 and the cover plate 2115, the measurement assembly 213 can reliably abut against the cover plate 2115, thus ensuring the alignment of the light emitter 2131 and the light receiver 2133 with the light transmission areas A1. As illustrated in FIG. 7, in this embodiment, after injection molding with the base plate 2115a, the light shielding part 2115b defines an emitting window and a receiving window which are spaced apart from each other, so as to reduce the interference between the emitting optical path and the receiving optical path. This structure, combined with the arrangement of the partition member 218, can further prevent the optical path interference between the light emitter 2131 and the light receiver 2133 in a gap between the measurement assembly 213 and the cover plate 2115, thus further improving the accuracy of blood pressure measurement. It can be understood that the partition member 218 can be defaulted.

As illustrated in FIG. 5, in this embodiment, the bearing member 2113 includes a frame body 2113a and a bottom cover 2113b, the bottom cover 2113b is disposed on a side of the frame body 2113a facing away from the cover plate 2115, and the bottom cover 2113b, the frame body 2113a and the cover plate 2115 enclose to define the accommodation cavity 211a. The bottom cover 2113b may be made of the same material as the frame body 2113a. In some embodiments, both the bottom cover 2113b and the frame body 2113a may be made of stainless steel, plastic, glass or ceramic. The material of the bottom cover 2113b may be different from that of the frame body 2113a. In some embodiments, the frame body 2113a may be a stainless steel metal injection molding member (MIM), and the bottom cover 2113b may be a ceramic or glass member.

The shape of the bottom cover 2113b can be adapted to the shape of the wrist, thus the blood pressure measurement module 210 can fit the wrist better. In some embodiment, the side of the bottom cover 2113b facing away from the cover plate 2115 can be machined into an arc surface, the surface of the bottom cover 2113b can better fit the user's wrist and improve the wearing comfort. It can be understood that because the function of the blood pressure measurement module 210 is relatively simple, its external dimension can be set relatively small to improve the external characteristics of the wearable device 10. In some embodiments, a width of the housing 211 of the blood pressure measurement module 210 can be close to a width of the strap 220, so as to improve the appearance characteristics of the wearable device 10 and avoid greatly influencing the bending of the strap 220 to reduce the wearing comfort.

Figure 10:
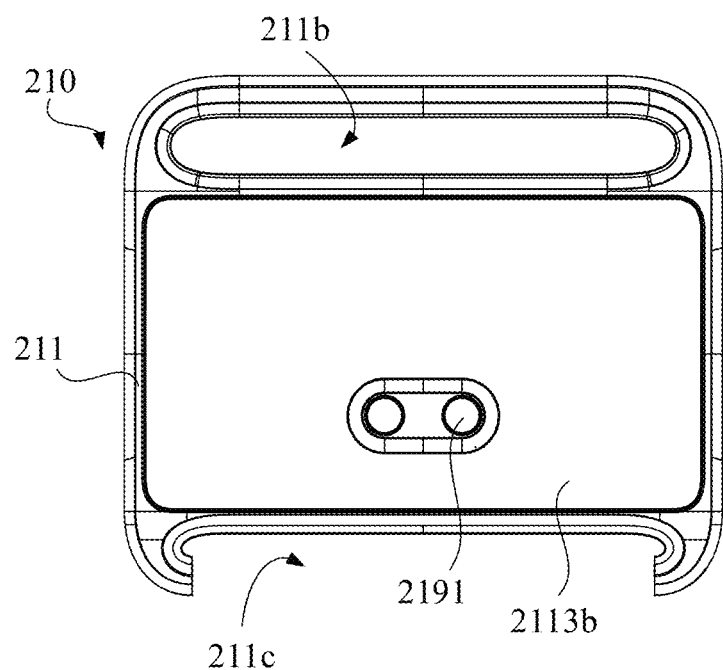
FIG. 10 illustrates a rear view of the blood pressure measurement module illustrated in FIG. 3.

As illustrated in FIG. 10, in the embodiment where the blood pressure measurement module 210 includes the battery 217, the blood pressure measurement module 210 may further include charging terminals 2191 electrically connected to the circuit board 215, and the charging terminals 2191 are exposed at a side of the bottom cover 2113b facing away from the emitting end of the light emitter 2131, and the charging terminals 2191 may be configured to connect an external charger to charge the battery 217 of the blood pressure measurement module 210. As illustrated in FIG. 8, the blood pressure measurement module 210 may include magnetic attraction members 2193, which are disposed in the accommodation cavity 211a and fixedly connected with the bottom cover 2113b or the frame body 2113a, and are configured to attract the charger to realize the reliable positioning of the blood pressure measurement module 210 on the charger, thus the charging terminals 2191 can form a reliable electrical connection with the charger.

In some embodiments, the blood pressure measurement module 210 may include sealing rings 2195, and the sealing rings 2195 are respectively sleeved on the charging terminals 2191. The bottom cover 2113b is provided with penetrating holes 2113c, and the charging terminal 2191 and the corresponding sealing ring 2195 pass through the corresponding penetrating holes 2113c, and the sealing ring 2195 seals the gap between the charging terminal 2191 and the bottom cover 2113b. Through an interference fit between the sealing ring 2195 and the penetrating hole 2113c, and an interference fit between the sealing ring 2195 and the charging terminal 2191, the gap between the charging terminal 2191 and the bottom cover 2113b can be effectively sealed, so as to improve the waterproof and dustproof performance of the blood pressure measurement module 210.

It can be understood that in other embodiments, the charging terminals 2191 can be replaced by a charging coil, so as to wirelessly charge the blood pressure measurement module 210 by using the charging coil, thereby improving the convenience of charging. In this embodiment, since the charging terminals 2191 and the penetrating holes 2113c are not required, the waterproof and dustproof performance of the blood pressure measurement module 210 can be improved. In some embodiments, the charging coil is spirally wound with copper wire, and the charging coil can be fixedly connected to the bottom cover 2113b with adhesive.

In other embodiments, the charging coil may be formed on the bottom cover 2113b by laser direct structuring (LDS) process to simplify the processing of the charging coil. In this embodiment, the charging coil may be formed on an inner surface of the bottom cover 2113b or on an outer surface of the bottom cover 2113b, that is, on a side of the bottom cover 2113b facing away from the cover plate 2115. Of course, the inner surface and the outer surface of the bottom cover 2113b can form charging coils through LDS process to improve the efficiency of wireless charging. In this embodiment, the charging coil is no longer limited to the planar area. For example, the charging coil can be completely arranged in the planar area of the bottom cover 2113b, or completely arranged in the curved area of the bottom cover 2113b, or can extend from the planar area of the bottom cover 2113b to the curved area of the bottom cover 2113b. This structural arrangement can make full use of the shape of the housing 211 to improve the structural compactness of the blood pressure measurement module 210, and further reduce the overall size of the blood pressure measurement module 210.

The technical features of the above-mentioned embodiments can be combined arbitrarily. In order to make the description concise, not all possible combinations of the technical features in the above-mentioned embodiments are described. However, as long as there is no contradiction between the combinations of these technical features, they should be considered as the scope recorded in this specification.

The above-mentioned embodiments only express several implementations of the present disclosure, and their descriptions are more specific and detailed, but they cannot be understood as limiting the scope of the present disclosure. It should be pointed out that for those skilled in the art, without departing from the concept of the present disclosure, several modifications and improvements can be made, which are within the scope of the protection of the present disclosure. Therefore, the scope of protection of the present disclosure should be based on the attached claims.

What is claimed is:

1. A blood pressure measurement module, configured to install on a strap of a wearable device, wherein the blood pressure measurement module comprises:
   a housing, provided with an accommodation cavity, the housing being configured to connect to the strap;
   a measurement assembly, configured to measure a blood pressure and comprising a light emitter and a light receiver, wherein the light emitter and the light receiver are disposed in the accommodation cavity, and the light receiver is configured to receive light emitted by the light emitter and reflected by a human body; and a wireless communication module, communicably connected to the measurement assembly, wherein the wireless communication module is configured to perform wireless communication connection with an external device or an electronic device of the wearable device;
wherein the housing comprises a bearing member and a cover plate, the cover plate covers an emitting end of the light emitter and a receiving end of the light receiver, the cover plate and the bearing member enclose to define the accommodation cavity, the cover plate comprises a base plate and a light shielding part connected to the base plate, the light shielding part defines light transmission areas of the base plate, and the light transmission areas cover the emitting end of the light emitter and the receiving end of the light receiver;
wherein the blood pressure measurement module further comprises a partition member, and the partition member is disposed between the cover plate and the measurement assembly and corresponds to the light transmission areas, and the partition member is configured to partition the emitting end of the light emitter and the receiving end of the light receiver; and
wherein the partition member comprises a first hole and a second hole arranged at intervals, a side of the partition member abuts against the cover plate, and another side of the partition member abuts against at least one of the light emitter and the light receiver, and the first hole corresponds to the emitting end of the light emitter and the second hole corresponds to the receiving end of the light receiver.

2. The blood pressure measurement module according to claim 1, wherein the base plate and the light shielding part are injection molded in two colors.

3. The blood pressure measurement module according to claim 1, wherein one of the light transmission areas is provided with an optical texture structure, and the optical texture structure covers the emitting end of the light emitter and is configured to gather light of the light emitter.

4. The blood pressure measurement module according to claim 3, wherein each of the light transmission areas is a closed area.

5. The blood pressure measurement module according to claim 3, wherein the light shielding part and the optical texture structure are disposed at a side of the base plate facing towards the light emitter.

6. The blood pressure measurement module according to claim 1, wherein one of the light transmission areas is provided with an optical texture structure covering the emitting end of the light emitter and is configured to gather light of the light emitter, and a vertical distance between the partition member and an appearance surface of the base plate is greater than a vertical distance between a tip of the optical texture structure and the appearance surface of the base plate.

7. The blood pressure measurement module according to claim 1, wherein the bearing member comprises a frame body and a bottom cover, the bottom cover is disposed on a side of the frame body facing away from the cover plate, and the bottom cover, the frame body and the cover plate enclose to define the accommodation cavity.

8. The blood pressure measurement module according to claim 7, wherein the blood pressure measurement module comprises a circuit board disposed in the accommodation cavity and between the cover plate and the bottom cover; and the light emitter and the light receiver are electrically connected to the circuit board.

9. The blood pressure measurement module of claim 8, wherein the blood pressure measurement module further comprises a battery and a charging coil; the battery is electrically connected to the circuit board and disposed in the accommodation cavity; and the charging coil is fixedly connected to the bottom cover.

10. The blood pressure measurement module according to claim 8, wherein the blood pressure measurement module further comprises a battery electrically connected to the circuit board and charging terminals electrically connected to the circuit board; and the battery is disposed in the accommodation cavity and the charging terminals are exposed at a side of the housing facing away from the emitting end of the light emitter.

11. The blood pressure measurement module according to claim 10, wherein the blood pressure measurement module further comprises sealing rings sleeved on the charging terminals correspondingly; the housing is provided with penetrating holes, the charging terminals and the sealing rings penetrate through the penetrating holes correspondingly, and each of the sealing rings seals a gap between a corresponding charging terminal and the housing.

12. The blood pressure measurement module according to claim 10, wherein the blood pressure measurement module comprises magnetic attraction members, the magnetic attraction members are disposed in the accommodation cavity and connected to the housing, and the magnetic attraction members are configured to attract a charger.

13. The blood pressure measurement module according to claim 1, wherein two opposite ends of the housing are provided with through holes, and the through holes are configured to thread the strap, thereby to make the blood pressure measurement module be slidably arranged on the strap.

14. The blood pressure measurement module according to claim 1, wherein an end of the housing is provided with a through hole, and another end of the housing is provided with an installation groove, and the installation groove is configured to connect the strap, and the through hole is configured to thread the strap.

15. A strap assembly, comprising:
a strap configured to connect an electronic device of a wearable device and a blood pressure measurement module detachably connected to the strap;
wherein the blood pressure measurement module comprises:
a housing, provided with an accommodation cavity, the housing being detachably connected to the strap;
a measurement assembly, configured to measure a blood pressure and comprising a light emitter and a light receiver, wherein the light emitter and the light receiver are disposed in the accommodation cavity, and the light receiver is configured to receive light emitted by the light emitter and reflected by a human body; and
a wireless communication module, communicably connected to the measurement assembly, wherein the wireless communication module is configured to perform wireless communication connection with an external device or the electronic device of the wearable device;
wherein the housing comprises a bearing member and a cover plate, the cover plate covers an emitting end of the light emitter and a receiving end of the light receiver, the cover plate and the bearing member enclose to define the accommodation cavity, the cover plate comprises a base plate and a light shielding part connected to the base plate, the light shielding part defines light transmission areas of the base plate, and the light transmission areas cover the emitting end of the light emitter and the receiving end of the light receiver;

wherein the blood pressure measurement module further comprises a partition member. and the partition member is disposed between the cover plate and the measurement assembly and corresponds to the light transmission areas, and the partition member is configured to partition the emitting end of the light emitter and the receiving end of the light receiver; and wherein one of the light transmission areas is provided with an optical texture structure covering the emitting end of the light emitter and is configured to gather light of the light emitter, and a vertical distance between the partition member, and an appearance surface of the base plate is greater than a vertical distance between a tip of the optical texture structure and the appearance surface of the base plate.

16. The strap assembly according to claim 15, wherein the light shielding part and the optical texture structure are disposed at a side of the base plate facing towards the light emitter.

17. The strap assembly according to claim 15, wherein the partition member comprises a first hole and a second hole arranged at intervals, a side of the partition member abuts against the cover plate, and another side of the partition member abuts against at least one of the light emitter and the light receiver, and the first hole corresponds to the emitting end of the light emitter and the second hole corresponds to the receiving end of the light receiver.

18. A wearable device, comprising:
an electronic device and a strap assembly connected to the electronic device, wherein the strap assembly comprises: a strap and a blood pressure measurement module connected to the strap, and the blood pressure measurement module comprises:
a housing, provided with an accommodation cavity and connected to the strap;
a measurement assembly, configured to measure a blood pressure and comprising a light emitter and a light receiver, wherein the light emitter and the light receiver are disposed in the accommodation cavity, and the light receiver is configured to receive light emitted by the light emitter and reflected by a human body; and
a wireless communication module, communicably connected to the measurement assembly, wherein the wireless communication module is configured to perform wireless communication connection with the electronic device;
wherein the housing comprises a bearing member and a cover plate, the cover plate covers an emitting end of the light emitter and a receiving end of the light receiver, the cover plate and the bearing member enclose to define the accommodation cavity, the cover plate comprises a base plate and a light shielding part connected to the base plate, the light shielding part defines light transmission areas of the base plate, and the light transmission areas cover the emitting end of the light emitter and the receiving end of the light receiver;
wherein the blood pressure measurement module further comprises a partition member, and the partition member is disposed between the cover plate and the measurement assembly and corresponds to the light transmission areas, and the partition member is configured to partition the emitting end of the light emitter and the receiving end of the light receiver; and
wherein the partition member comprises a first hole and a second hole arranged at intervals, a side of the partition member abuts against the cover plate, and another side of the partition member abuts against at least one of the light emitter and the light receiver, and the first hole corresponds to the emitting end of the light emitter and the second hole corresponds to the receiving end of the light receiver.

19. The wearable device according to claim 18, wherein one of the light transmission areas is provided with an optical texture structure covering the emitting end of the light emitter and is configured to gather light of the light emitter, and a vertical distance between the partition member, and an appearance surface of the base plate is greater than a vertical distance between a tip of the optical texture structure and the appearance surface of the base plate.

20. The wearable device according to claim 18, wherein the emitting end of the light emitter faces away from a user's wrist when the electronic device is worn on the user's wrist through the strap;
wherein the bearing member comprises a frame body and a bottom cover, the bottom cover is disposed on a side of the frame body facing away from the cover plate, and the bottom cover, the frame body and the cover plate enclose to define the accommodation cavity; and
wherein the blood pressure measurement module comprises a circuit board disposed in the accommodation cavity and between the cover plate and the bottom cover, and the light emitter and the light receiver are electrically connected to the circuit board.

* * * * *